United States Patent
Li et al.

(10) Patent No.: US 11,377,426 B2
(45) Date of Patent: Jul. 5, 2022

(54) PROCESSES TO PRODUCE ELAGOLIX

(71) Applicant: SUZHOU PENGXU PHARMATECH CO., LTD., Wujiang Suzhou (CN)

(72) Inventors: Pixu Li, Suzhou (CN); Peng Wang, Suzhou (CN); Xiangyong Gu, Suzhou (CN); Hailong Yang, Suzhou (CN); Zhong Wang, Suzhou (CN); Qianghua Jiang, Suzhou (CN); Yuanhua Liu, Suzhou (CN); Hui Xia, Suzhou (CN)

(73) Assignee: SUZHOU PENGXU PHARMATECH CO., LTD., Wujiang Suzhou (CN)

( * ) Notice: Subject to any disclaimer, the term of this patent is extended or adjusted under 35 U.S.C. 154(b) by 295 days.

(21) Appl. No.: 16/770,035

(22) PCT Filed: Dec. 3, 2018

(86) PCT No.: PCT/US2018/063682
§ 371 (c)(1),
(2) Date: Jun. 4, 2020

(87) PCT Pub. No.: WO2019/112968
PCT Pub. Date: Jun. 13, 2019

(65) Prior Publication Data
US 2021/0214318 A1 Jul. 15, 2021

(30) Foreign Application Priority Data

Dec. 5, 2017 (CN) .......................... 201711263255.7
Jan. 17, 2018 (CN) .......................... 201810042494.8
Aug. 17, 2018 (CN) .......................... 201810941650.4
Sep. 21, 2018 (CN) .......................... 201811104129.1

(51) Int. Cl.
*C07D 239/54* (2006.01)
*B01J 23/44* (2006.01)
*B01J 25/02* (2006.01)

(52) U.S. Cl.
CPC ............ *C07D 239/54* (2013.01); *B01J 23/44* (2013.01); *B01J 25/02* (2013.01)

(58) Field of Classification Search
CPC ......... B01J 23/44; B01J 25/02; C07C 249/08; C07C 251/47; C07C 45/004; C07C 47/55; C07C 209/62; C07C 211/27; C07C 269/00; C07C 271/14; C07C 45/008; C07D 239/54; C07D 279/06; C07B 2200/09
See application file for complete search history.

(56) References Cited

U.S. PATENT DOCUMENTS 5,977,414 A 11/1999 Okabe et al.
7,419,983 B2 9/2008 Guo et al.
2005/0131032 A1 6/2005 Sit et al.
2012/0059179 A1 3/2012 Yu
2017/0320836 A1 11/2017 Gallagher et al.

FOREIGN PATENT DOCUMENTS

| WO | 03/065989 A2 | 8/2003 | |
|---|---|---|---|
| WO | 2005/007165 A1 | 1/2005 | |
| WO | WO-2005007165 A1 * | 1/2005 | ........... C07D 239/52 |
| WO | 2008/152089 A1 | 12/2008 | |
| WO | 2009/062087 A1 | 5/2009 | |
| WO | 2016144703 A1 | 9/2016 | |

OTHER PUBLICATIONS

Yuskovets et al., ("Azines and Azoles: CXXII. New Regioselective Synthesis of 1-Substituted 6-Alkyluracils" Russian Journal of General Chemistry, vol. 75, No. 1, pp. 1608-3350, Published 2005. As cited in the IDS filed Nov. 18, 2021) (Year: 2005).*
Le Wang et al., "Regioselective formylation of 1,3-disubstituted benzenes through in situ lithiation", Tetrahedron Letters 54 (2013) 6053-6056.
Third party observation submitted on Jun. 22, 2021 for EP related Patent Application No. 18885965.6.
European Application No. 18885965.6, Extended European Search Report dated Jul. 30, 2021, 14 pages.
Yuskovets V N et al., "Azines and Azoles: CXXII. New Regioselective Synthesis of 1-Substituted 6-Alkyluracils" Russian Journal of General Chemistry, vol. 75, No. 1, 2005, pp. 1608-3350.
Pontillo J et al., "Efficient Synthesis of Bicyclic Oxazolino and Thiazolino [3,2-c] Pyrimidine-5, 7-diones and its Application to the Synthesis of GnRH Antagonists", Bioorganic & Medicinal Chemistry Letters, Elsevier, vol. 15, No. 5, 2005, pp. 1407-1411.
Supplemental European International Search Report dated Apr. 13, 2021 for related EP Application No. EP18885965.
Anonymous: "Process for the preparation of 1-(2-fluoro-6-(trifluoromethyl)benzyl}urea and (2-fluoro-6-(trifuloromethyl)phenyl}urethan amine hydrochloride", ip.com Journal, Sep. 14, 2017 (Sep. 14, 2017).
Taiwan Application No. 11021139410, Taiwan Office action dated Nov. 23, 2021, 5 pages.
International Search Report and Written Opinion dated Mar. 27, 2019 for related PCT Application No. PCT/US18/63682.
International Preliminary Report on Patentability dated Jun. 9, 2020 for related PCT Application No. PCT/US18/63682.
Indian Application No. 202047028492, Indian Examination Search Report dated Dec. 11, 2021, 6 pages.

* cited by examiner

*Primary Examiner* — Yevgeny Valenrod
*Assistant Examiner* — Blaine G Doletski
(74) *Attorney, Agent, or Firm* — MagStone Law, LLP; Enshan Hong

(57) ABSTRACT

The present invention relates to a scalable process for the making of elagolix, its salts and the process of intermediate compounds.

20 Claims, No Drawings

PROCESSES TO PRODUCE ELAGOLIX

RELATED APPLICATIONS

This is a U.S. national stage of international application No. PCT/US2018/063682 filed on Dec. 3, 2018, which claims priority to Chinese Patent Application Nos. 201711263255.7 filed on Dec. 5, 2017, 201810042494.8 filed on Jan. 17, 2018, 201810941650.4 filed on Aug. 17, 2018, and 201811104129.1 filed on Sep. 21, 2018 with the China National Intellectual Property Administration (CNIPA), all of which are incorporated herein by reference in their entirety.

BACKGROUND OF THE INVENTION

1. Field of the Invention

The present invention relates to process for preparing the compound of formula III, compound of formula IV, compound of formula V, compound of formula VI, compound of formula VIII, compound of formula IX, compound of formula XIV, compound of formula X, compound of formula XII, compound of formula XIII, and elagolix sodium, a gonadotropin-releasing hormone (GnRH) receptor antagonist indicated for the management of moderate to severe pain associated with endometriosis.

III

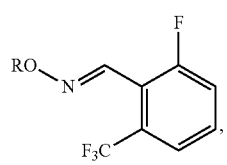

R = H, methyl or ethyl

IV

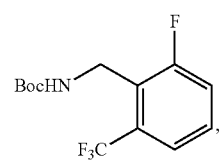

V

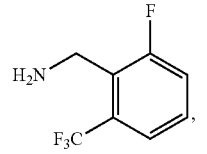

VI

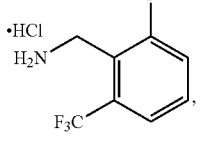

VIII

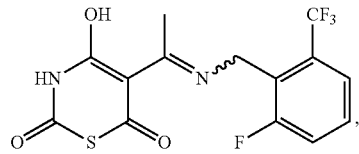

IX

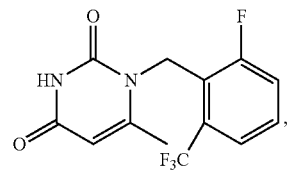

X

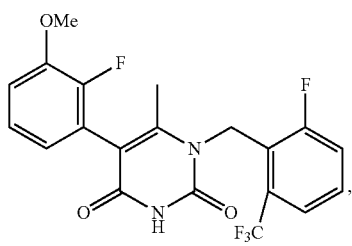

XIV

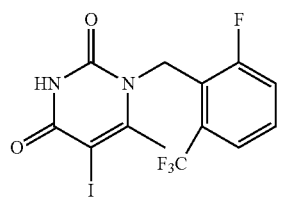

XII

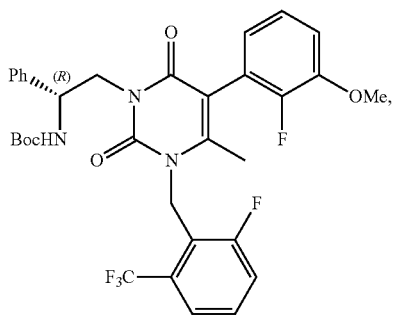

XIII

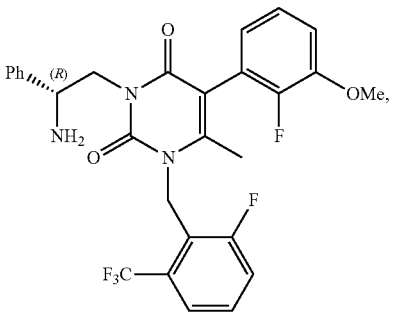

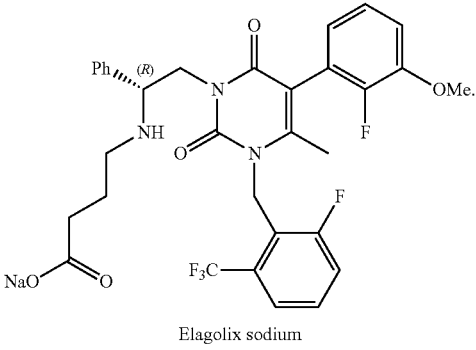

Elagolix sodium

2. Description of the Related Art

Orilissa (elagolix sodium; previously known as NBI-56418 or ABT-620) is a gonadotropin-releasing hormone antagonist (GnRH antagonist) medication which is used in the treatment of pain associated with endometriosis in women. Orilissa is also under development for the treatment of uterine fibroids in women.

Orilissa was approved by the FDA for the treatment of endometriosis-associated pain in the United States on 23 Jul. 2018. It was the first new medication to be approved by the FDA for the treatment of endometriosis in more than a decade. Elagolix is the first and currently the only marketed member of a new class of GnRH modulators, which is described as "second-generation" due to their non-peptide and small-molecule nature and oral activity.

The preparation of elagolix was disclosed in International Patent Application WO2005/007165 A1:

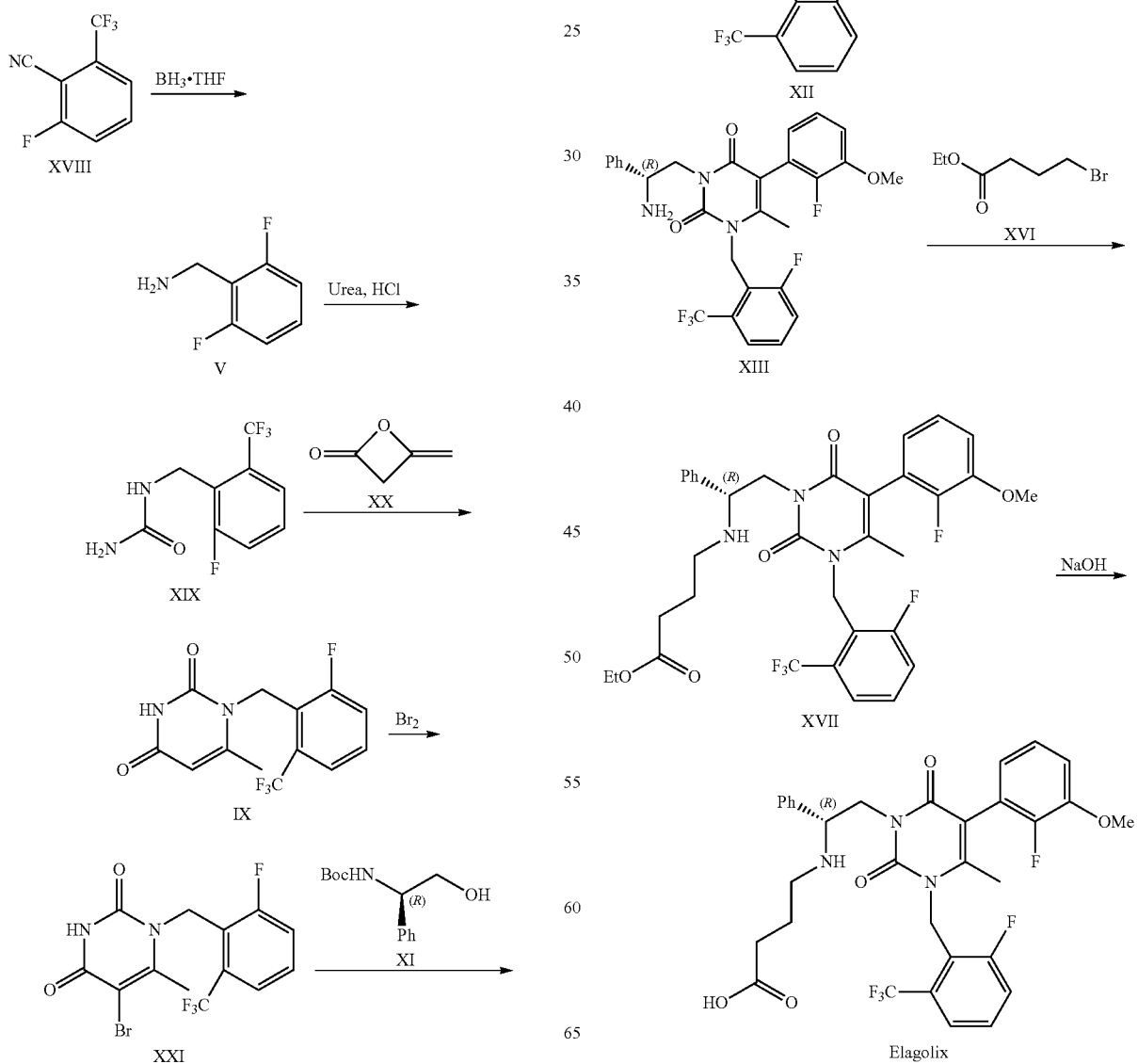

Compound V, IX, XII and XIII are key intermediates for the preparation of elagolix. Another synthetic route to the Compound XIII from the Compound XXII was also disclosed:

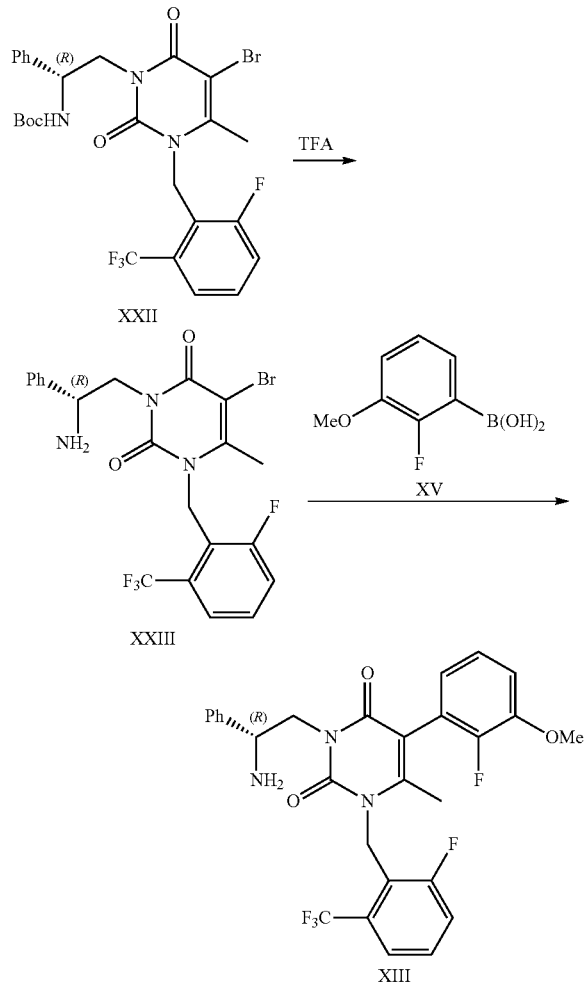

In WO2005/007165 A1, the technical solution for the preparation of compound V requires the use of the expensive starting material XVIII, as compound XVIII is not a commercially available bulk material. For the preparation of compound IX, compound V reacts with urea to produce compound XIX; compound XIX is treated with 15 equivalents of acetyl ketene, sodium iodide, and chlorotrimethylsilane; the yield of compound IX from compound V is 58%, resulting in an uneconomic synthetic process. For the preparation of compound XIII, two routes were disclosed. Both of the routes start from compound XXII, requiring a large amount of catalyst for the Suzuki coupling reaction.

Another route for the preparation of elagolix was disclosed in WO2009/062087 A1: In WO2009/062087 A1, the preparation of compound V is same as the method in WO2005/007165 A1. For the preparation of compound IX, the compound XIX reacts with tert-butyl acetoacetate catalyzed by p-toluenesulfonic acid. The yield of compound IX from compound V is 46%, which is undesirably low. For the preparation of compound XII, compound X reacts with compound XXV, the byproduct of which is methanesulfonic acid. The residue of methanesulfonic acid may lead to the formation of methanesulfonic acid ester, which is a potential genotoxic impurity. For the preparation of compound XIII, methanesulfonic acid is also used, which may bring the same potential genotoxic impurity problem.

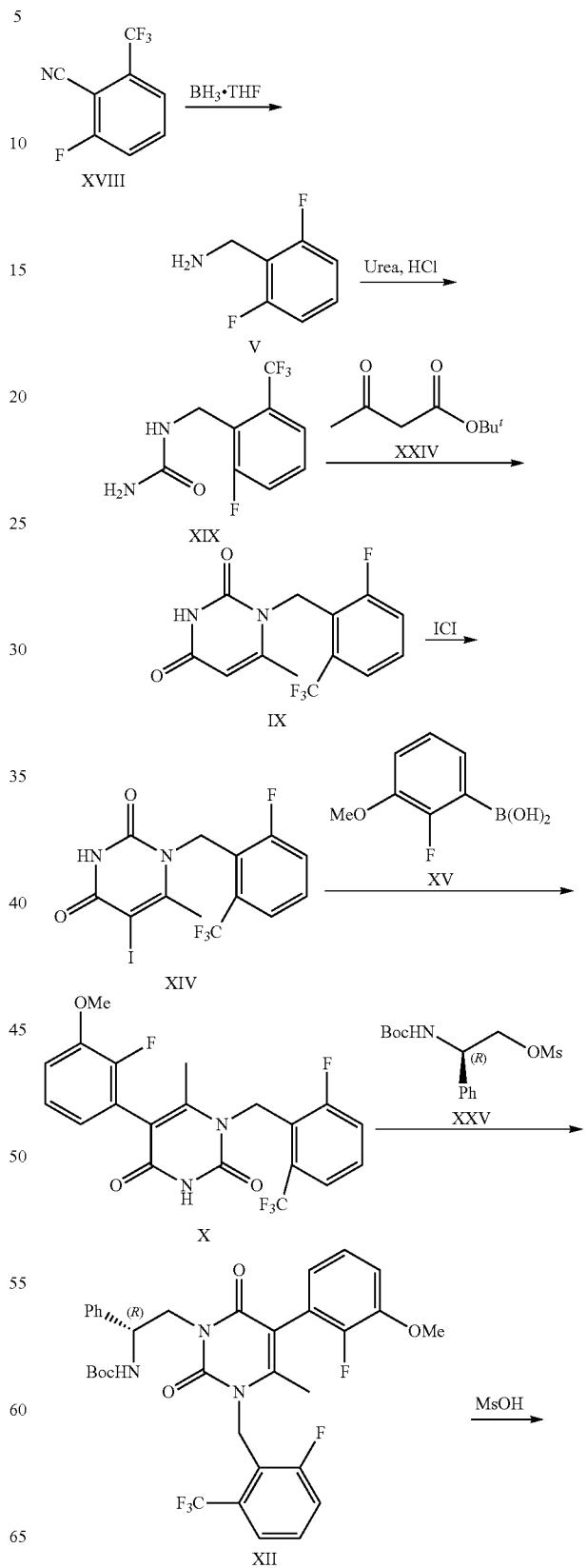

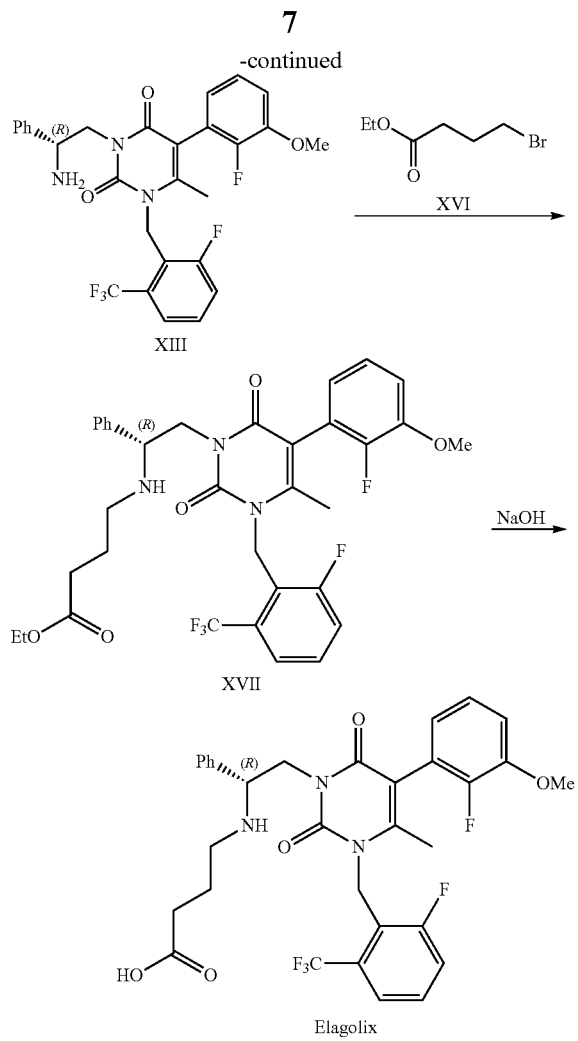

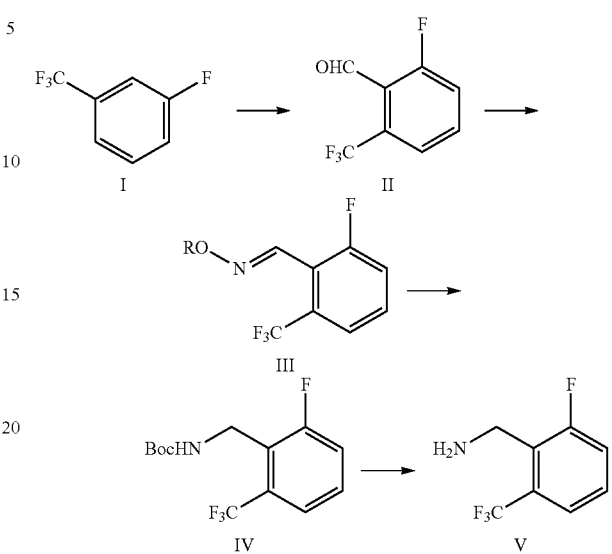

wherein R is a substituent selected from the group consisting of H, methyl or ethyl.

In a specific embodiment, the reaction conditions for each reaction step are detailed below:

Synthesis of the compound of formula III from the compound of formula I and compound of formula II:

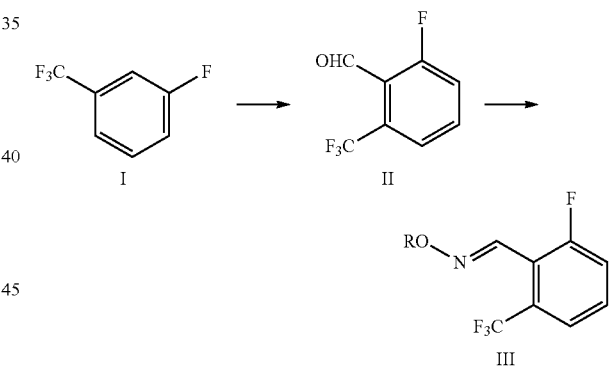

Compound I is a commercially available bulk material, and the compound III can be prepared efficiently by continuous reaction without separation of compound II.

The compound I reacts with DMF in an organic solvent in the presence of organolithium reagents and amine additives to prepare compound II. Preferably, the organic solvent is selected from tetrahydrofuran, methyl tetrahydrofuran, n-heptane, n-hexane, toluene, xylene and mixtures thereof. Preferably, the solvent is tetrahydrofuran. Preferably, the amine additive is one or more of tetramethylethylenediamine, diisopropylamine, diethylamine, di-sec-butylamine or pentamethyldiethylenetriamine. Preferably, the amine additives are tetramethylethylenediamine and diisopropylamine. Preferably, the organolithium reagent is one of n-butyl lithium, tert-butyl lithium, isobutyl lithium, lithium diisopropylamide, lithium bis (trimethylsilyl) amide. Preferably, the organolithium reagent is n-butyl lithium. Preferably, the reaction temperature is −60~−80° C. The com- Elagolix Technical Problem: The current processes to the intermediates of elagolix, compound V and compound IX require high raw material costs, and results in low yield. For compound XII and compound XIII, the process cost is high and there is the problem of a genotoxic impurity. A scalable preparation route is needed to overcome these problems for large-scale production.

SUMMARY OF THE INVENTION

It is the object of the present invention to provide a cost effective and scalable process for the preparation of elagolix and the seven intermediates: compound of formula III, compound of formula IV, compound of formula V, compound of formula VIII, compound of formula IX, compound of formula XIV, compound of formula X, compound of formula XII, and compound of formula XIII One purpose of the present application is to provide a preparation of compound III, compound IV and compound V.

A further purpose of the present application is to provide a method to prepare the compound VIII and compound IX.

A further purpose of the present application is to provide a method to prepare the compound X.

A further purpose of the present application is to provide a method to prepare the compound XII and compound XIII A further purpose of the present application is to provide a process to prepare of elagolix and elagolix sodium.

The present application provides a process for the preparation of compound III, compound IV and compound V:

pound II reacts with alkoxy amine or hydroxylamine hydrochloride at 10~50° C. in the presence of a base to prepare compound III. Preferably, the base is selected from sodium hydroxide, potassium hydroxide, triethylamine, N,N-diisopropylethylamine, sodium carbonate, potassium carbonate, and sodium bicarbonate. More preferably, the base is sodium bicarbonate.

Because of the low boiling point and volatility of compound II, it is used in the preparation of Compound III directly without separation from the solution.

Synthesis the compound of formula IV from the compound of formula III:

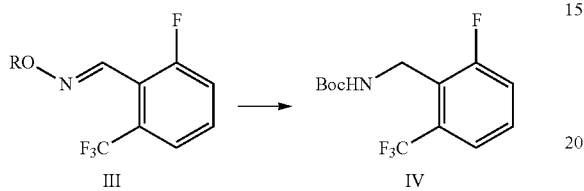

The compound III reacts with di-tert-butyl dicarbonate in an alcoholic solvent at 10~70° C. in the presence of a transition-metal catalyst under hydrogen atmosphere to prepare compound IV. Preferably, the alcoholic solvent is selected from methanol, ethanol, isopropanol and mixtures thereof. Preferably, the solvent is methanol. Preferably, the transition-metal catalyst is selected from Raney Ni or Pd/C. More preferably, the transition-metal catalyst is Raney nickel, and the hydrogen pressure is 0.1~5.0 MPa, more preferably, the hydrogen pressure is 0.2~0.5 MPa. Preferably, the reaction temperature is 20~40° C.

Synthesis the compound of formula V from the compound of formula IV:

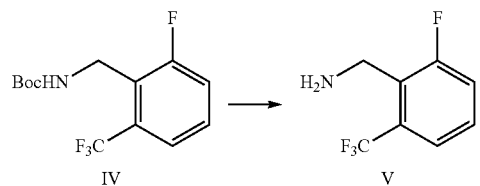

The compound IV reacts in the presence of an acid at 10~70° C. to prepare compound V or its salt compound VI. Preferably, the acid is hydrochloric acid. Preferably, the reaction temperature is 20~40° C.

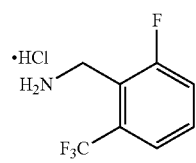

The compound III can be reduced directly with Raney Ni and $H_2$ to prepare compound V. However, such a process leads to the formation of impurity A. It is found that the addition of di-tert-butyl dicarbonate can effectively control the formation of impurity A. Further, we unexpectedly found that this method can effectively control the formation of impurity B. Impurity B has similar structure with compound V, which has a greater adverse impact to the final product quality. This improved method can effectively improve the final product quality by reducing the presence of impurities A and B.

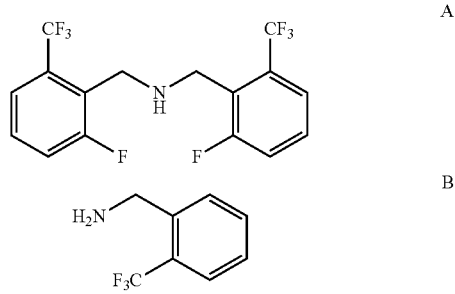

Compared with the prior art, the method has the following advantages:

1. The reaction conditions are mild. The explosive reagents such as boron hydride or Zn powder are not needed, so it is more environmentally-friendly and safe.

2. Continuous reaction reduces the loss of product resulting from product separation, and increases production efficiency.

3. Impurity formation is effectively reduced.

4. Inexpensive commercially available starting material is used in the process, resulting in reduced raw material cost.

The present application provides a process for the preparation of compound IX from compound VIII:

In a specific embodiment, the reaction conditions for each reaction step are detailed below: Synthesis the compound of formula IX from the compound of formula VIII:

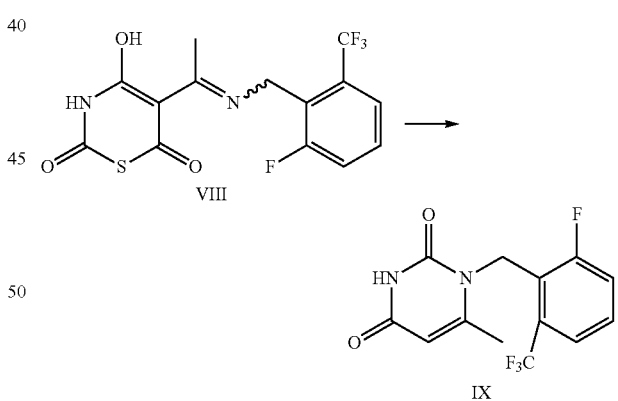

The compound VIII reacts in an organic solvent at 50~200° C. to prepare compound IX. Preferably, the organic solvent is selected from dimethylformamide, dimethylacetamide, acetonitrile, n-butanol, tert-butanol, 1,4-dioxane, dimethyl sulfoxide, N-methylpyrrolidone, sulfolane and mixtures thereof. Preferably, the organic solvent is dimethylformamide, N-methylpyrrolidone. More preferably, the organic solvent is dimethylformamide. Preferably, the reaction temperature is 80~160° C.

Synthesis of the compound of formula VIII from the compound of formula V and the compound of formula VII:

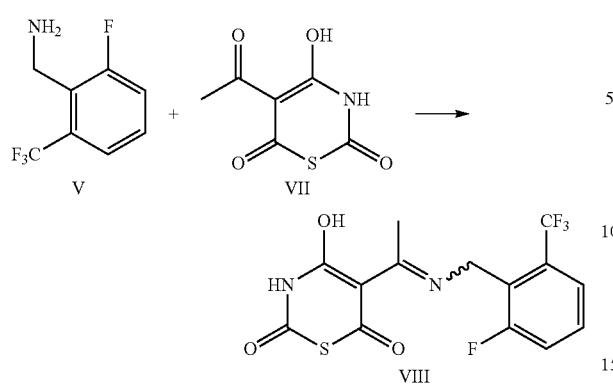

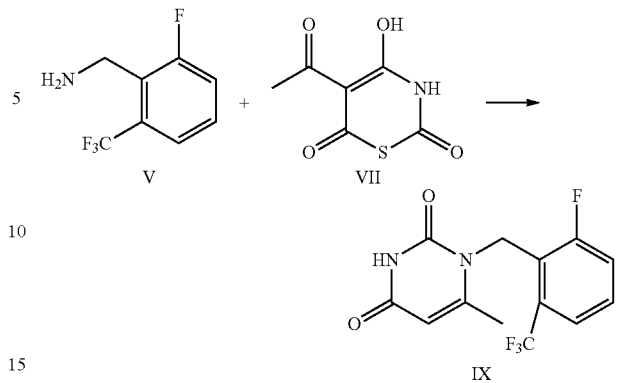

Compound VII can be readily prepared from malonic acid and potassium thiocyanate in acetic acid and acetic anhydride.

The compound V reacts with compound VII in an organic solvent at 50~200° C. to prepare compound VIII. Preferably, the organic solvent is selected from dimethylformamide, dimethylacetamide, acetonitrile, tetrahydrofuran, methyl tetrahydrofuran, isopropanol, n-butanol, tert-butanol, dioxane, dimethyl sulfoxide, N-methyl pyrrolidone, cyclobutanone and mixtures thereof. More preferably, the organic solvent is isopropanol. Preferably, the molar equivalence of compound VII is between 0.8 and 5. Preferably, the molar equivalence of compound VII is between 1 and 3. Preferably, the reaction temperature is 80~160° C.

Synthesis of the compound of formula VIII from the compound of formula VI and the compound of formula VII:

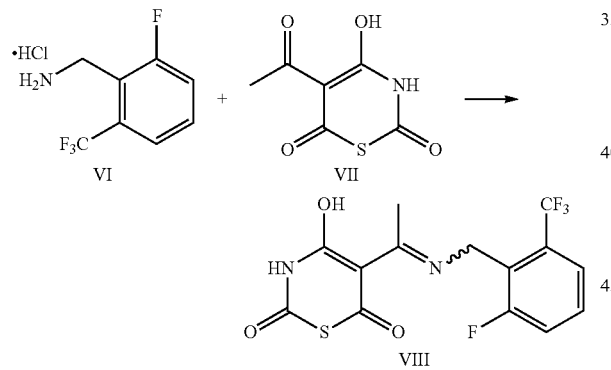

The compound VI reacts with compound VII in an organic solvent at 50~200° C. in the presence of a base to prepare compound VIII. Preferably, the base is selected from sodium hydroxide, potassium hydroxide, triethylamine, N,N-diisopropylethylamine, sodium carbonate, potassium carbonate, and sodium bicarbonate. More preferably, the base is sodium hydroxide. Preferably, the organic solvent is selected from dimethylformamide, dimethylacetamide, acetonitrile, tetrahydrofuran, methyl tetrahydrofuran, isopropanol, n-butanol, tert-butanol, dioxane, dimethyl sulfoxide, N-methyl pyrrolidone and cyclobutanone. More preferably, the organic solvent is isopropanol. Preferably, the molar equivalence of compound VII is between 0.8 and 5. More preferably, the molar equivalence of compound VII is between 1 and 3. Preferably, the reaction temperature is 80~160° C.

Synthesis of the compound of formula IX from the compound of formula V and the compound of formula VII:

The compound V reacts with compound VII in an organic solvent at 50~200° C. to prepare compound IX. Preferably, the organic solvent is selected from dimethylformamide, dimethylacetamide, acetonitrile, tetrahydrofuran, methyl tetrahydrofuran, isopropanol, n-butanol, tert-butanol, dioxane, dimethyl sulfoxide, N-methyl pyrrolidone and cyclobutanone. More preferably, the organic solvent is dimethylformamide. Preferably, the molar equivalence of compound VII is between 1 and 10. Preferably, the molar equivalence of compound VII is between 1 and 3. Preferably, the reaction temperature is 100~150° C.

Compared with the prior art, the method has the following advantages:
1. The process is efficient and atom-economic.
2. The yield of the process is high. The cost of synthesizing elagolix and elagolix sodium is greatly reduced.
3. The workup of the process is simple, the impurity removal is facile, and the purity of the product is high.

The present invention provides a process for the preparation of compound X:

In a specific embodiment, the reaction conditions for each reaction step are detailed below: Synthesis of the compound of formula X from the compound of formula IX:

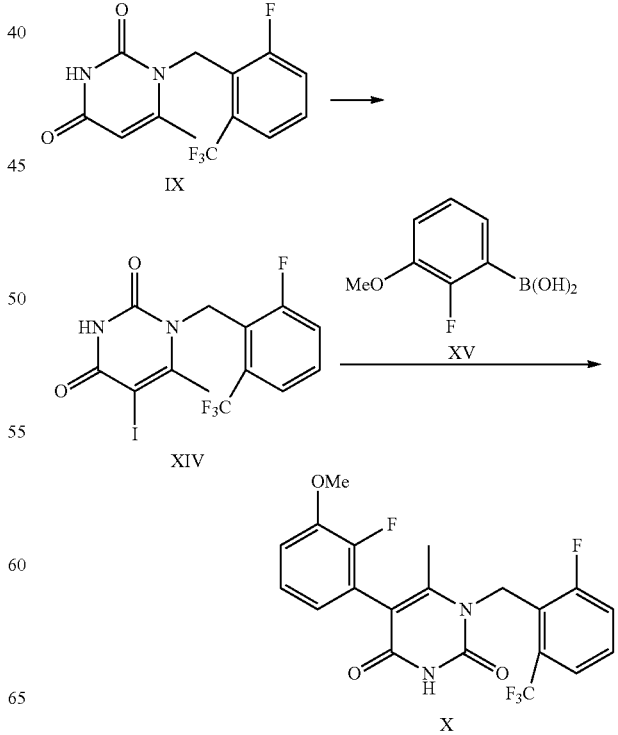

The compound of formula IX reacts with N-iodosuccinimide to prepare the compound of formula XIV. The compound of formula XIV reacts with the compound of formula XV to produce the compound of formula X using methanesulfonato[tri(tert-butyl) phosphine (2'-amino-1,1'-biphenyl-2-yl)] palladium (II) as the catalyst.

Compared with the prior art, the present method has the following advantages:
1. N-iodosuccinimide is easy to handle in production.
2. Methanesulfonato[tri (tert-butyl) phosphine (2'-amino-1, 1'-biphenyl-2-yl)] palladium (II) that is used as the catalyst is less air and moisture sensitive than the combination of Pd(OAc)$_2$ and tri-tert-butylphosphine ligand, which makes the reaction more robust.

The present application provides a process for the preparation of compound XII and compound XIII:

In a specific embodiment, the reaction conditions for each reaction step are detailed below: Synthesis of the compound of formula XII from the compound of formula X and the compound of formula XI:

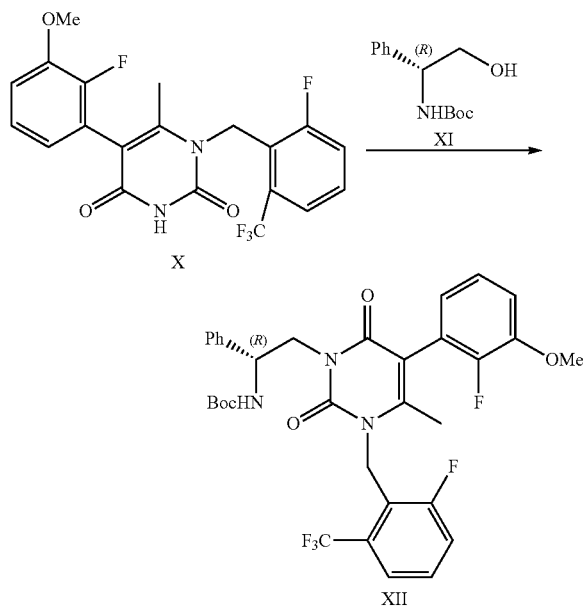

The compound of formula X reacts with the compound of formula XI under Mitsunobu reaction conditions in the presence of an organic solvent to prepare compound XII. Preferably, the organic solvent is selected from dichloromethane, toluene, 1,4-dioxane, tetrahydrofuran, methyl tetrahydrofuran and mixtures thereof. More preferably, the organic solvent is tetrahydrofuran.

Synthesis of the compound of formula XIII from the compound of formula XII:

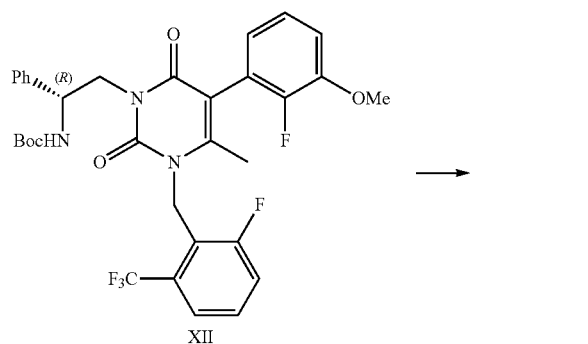

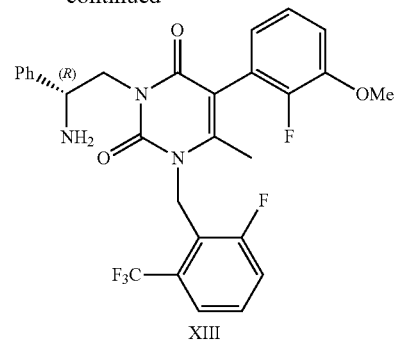

The compound of formula XII reacts under acidic conditions to prepare the compound of formula XIII Preferably, the acid is selected from methanesulfonic acid, hydrochloric acid, sulfuric acid, trifluoroacetic acid and mixtures thereof. Preferably, the acid is hydrochloric acid. Preferably, the reaction temperature is 50~60° C.

Synthesis the compound of formula XIII from the compound of formula X and the compound of formula XI:

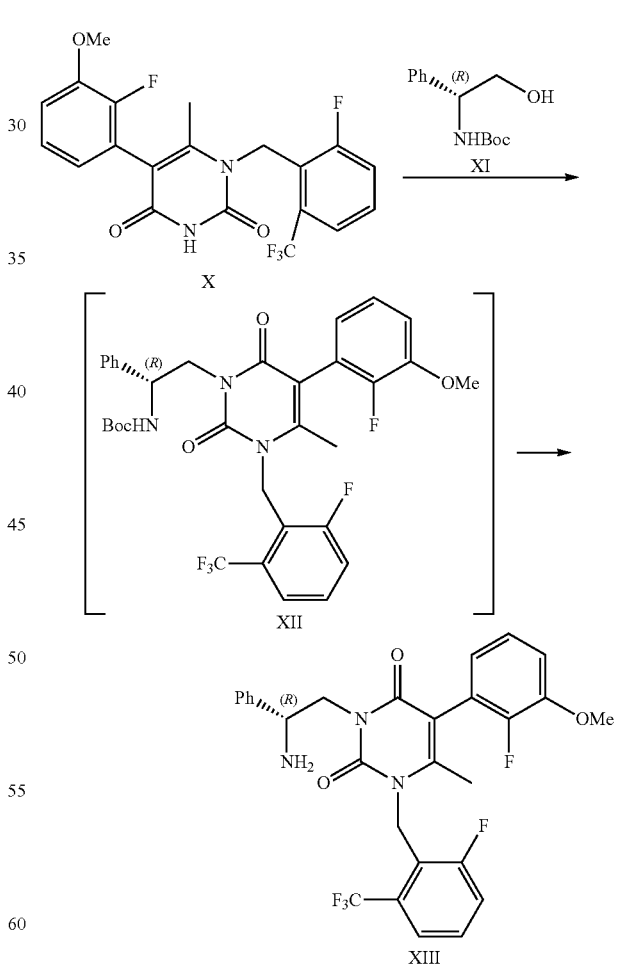

The compound of formula XIII can be prepared from the compound of formula X and the compound of formula XI in telescope or continuous reaction without the separation of compound XII.

Compared with the prior art, the present method has the following advantages:
1. Simplified reaction process, suitable for large-scale continuous reaction.
2. Avoid the use of potential genotoxic substances in the reaction process, making the process environmentally greener and safer.

DETAILED DESCRIPTION OF THE PRESENTLY PREFERRED EMBODIMENTS

Example

Example 1: Synthesis of Compound II

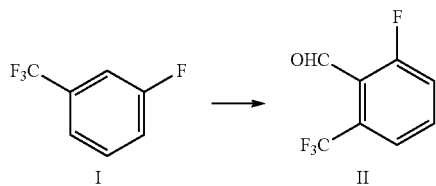

To a round-bottom flask were added compound I (20 g), tetramethylethylenediamine (15.6 g), diisopropylamine (0.6 g) and THF (200 mL). The mixture was cooled to −60~78° C. n-BuLi solution in hexanes (53.5 mL, 2.5 M) was added at −60~78° C. The reaction mixture was stirred at −60~78° C. for 1 h. DMF (13.4 g) was added at −60~78° C. After completion of the reaction, the reaction mixture was quenched with saturated $NH_4Cl$ solution (100 mL). The layers were separated. The organic phase was concentrated under vacuum. The crude material was purified by silica gel column chromatography eluting with hexane to get compound II as yellow oil (1.1 g, 4.5% yield, 99.0% purity).

$^1$H NMR (400 MHz, DMSO-d6) δ 10.46 (s, 1H) 7.71 (m, 1H), 7.64 (d, J=7.6 Hz, H), 7.44 (t, J=9.2 Hz, 1H).

Example 2: Synthesis of Compound III

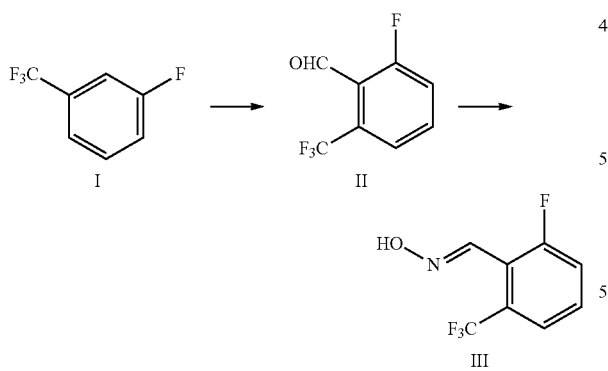

To a 100 L reactor were added THF (25 L), compound I (2.5 Kg), tetramethylethylenediamine (1.95 Kg) and diisopropylamine (77.5 g). The mixture was cooled to −60~−78° C. n-BuLi solution in hexanes (4.55 Kg, 2.5 M) was added at −60~−78° C. After the reaction mixture was stirred at −60~−78° C. for 1 h, DMF (1.68 Kg) was added at −60~−78° C. After completion of the reaction, the reaction mixture was warmed to −40~−20° C. The reaction mixture was poured into 20% AcOH aqueous solution. The layers were separated. The organic layer was added hydroxylamine hydrochloride (1.27 Kg) and sodium bicarbonate (1.02 Kg). The reaction mixture was stirred at 15~25° C. for 1 h. After the completion of the reaction, the reaction mixture was added HCl solution. The layers were separated. The product was crystallized with $EtOH/H_2O$ to give the product as off-white solid (2.27 Kg, 72% yield, 99.3% purity).

$^1$H NMR (400 MHz, DMSO-d6) δ 11.94 (s, 1H), 8.22 (dd, $^1$J=4.0 Hz, $^2$J=2.0 Hz, 1H), 7.68-7.63 (m, 3H).

Mass: $[M+H]^+$: 208.1;

Example 3: Synthesis of Compound IV

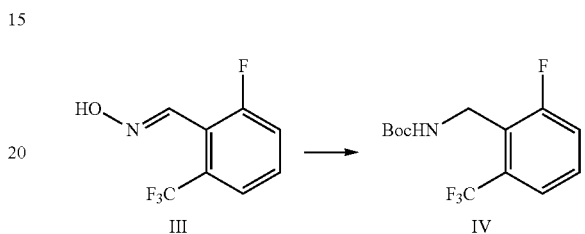

To a 20 L reactor were added MeOH (7.1 Kg), Raney Ni (100 g), di-tert-butyl dicarbonate (1.06 Kg) and compound III (500 g), the reactor was degassed three times and refilled with $H_2$ (0.3 MPa). The mixture was stirred at 2040° C. under $H_2$ (0.1-0.3) MPa. After completion of the reaction, the reaction mixture was filtered to remove Raney Ni. 1/25 of the filtrate was concentrated to dryness. The crude product was purified by silica gel column chromatography eluting with heptane/EA to give the product as a white solid (19.01 g, 95.05% yield).

$^1$H NMR (400 MHz, $CDCl_3$) δ 7.47 (d, J=8.0 Hz, 1H), 7.43-7.38 (m, 1H), 7.32-7.29 (m, 1H), 4.56 (d, J=6.8 Hz, 1H), 1.45 (s, 9H).

Mass: $[M-^tBu+H]^+$: 238.1;

Example 4: Synthesis of Compound VI

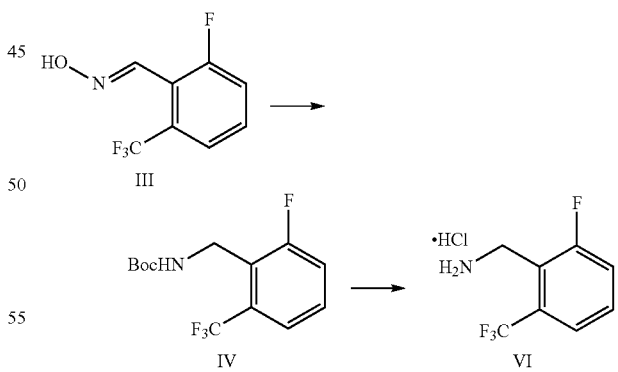

To a 20 L reactor were added MeOH (7.1 Kg), Raney Ni (100 g), di-tert-butyl dicarbonate (1.06 kg) and compound III (500 g). The reactor was degassed three times and refilled with $H_2$ (0.3 MPa). The mixture was stirred at 20~40° C. under $H_2$ (0.1~0.3 MPa). After completion of the reaction, the reaction mixture was filtered to remove Raney Ni. The filtrate was concentrated to 1.5 L, and then added 30% HCl in EtOH (535 g). The mixture was stirred at 30~40° C. for 3 h. After the completion of the reaction, the solvent was exchanged to IPAC. The resulting suspension was filtered to give the product as a white solid (482 g, 87% yield). HPLC showed the ratio of compound VI, impurity A and impurity B was 99.9:0.1:0.

Mass: [M+H]$^+$: 194.1;

Example 5: Synthesis of Compound V

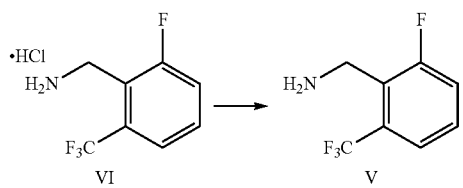

To a mixture of H$_2$O (2 L), MTBE (1.5 L) and compound VI (475 g in a 5 L reactor was added 25% NaOH (331 g) dropwise. After the reaction complete, the layers were separated. The aqueous layer was extracted with MTBE (1.5 L). The combined organic phase was washed with H$_2$O and concentrated to dryness. The product was obtained by vacuum distillation as colorless oil (367.9 g, 92.1% yield).

Mass: [M+H]$^+$: 194.1;

Example 6: Synthesis of Compound V

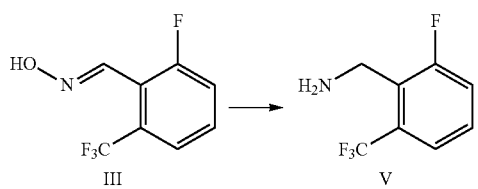

To a 2 L reactor was added MeOH (1 L), Raney Ni (40 g) and compound III (200 g). The reactor was degassed three times and refilled with H$_2$ (3.0~4.0 MPa). The mixture was stirred at 60~70° C. under H$_2$ (2.0-3.5 MPa). After completion of the reaction, the reaction mixture was filtered to remove Raney Ni. HPLC showed the ratio of compound V, impurity A and impurity B was 90.2:0.9:8.9.

Example 7: Synthesis of Compound V

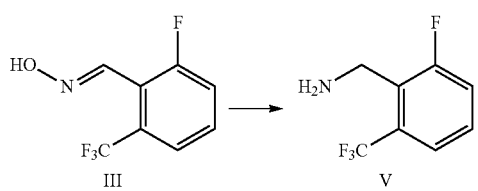

To a 250 mL reactor was added MeOH (100 mL), Pd/C (1 g), HCl (8 mL) and compound III (10 g). The reactor was degassed three times and refilled with H$_2$. The mixture was stirred at 60~70° C. under H$_2$ (2.0~3.0 MPa). After completion of the reaction, HPLC showed the ratio of compound V, impurity A and impurity B was 97.7:0.1:2.2.

Example 8: Synthesis of Compound VIII

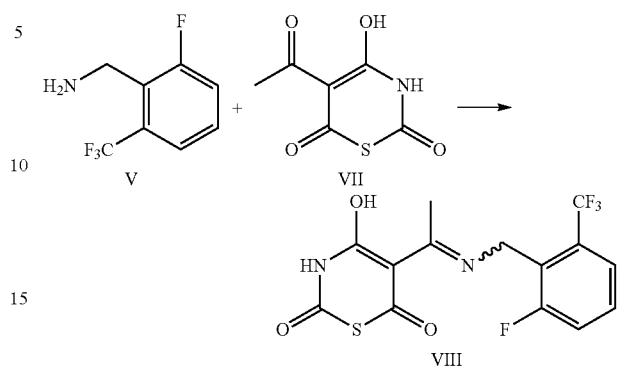

To a 100 mL round bottom flask was added isopropanol (50 mL), compound V (5 g) and compound VII (5.33 g), the reaction mixture was heated to 80~90° C. for 3 h. After completion of the reaction, H$_2$O (100 mL) was added to the reaction mixture. The mixture was extract with DCM. The organic phase was concentrated. The crude product was purified by silica gel column chromatography to give the product as a yellow solid (9.2 g, 98% yield, 98.0% purity).

1H NMR (400 MHz, DMSO) δ 12.91 (s, 1H), 11.66 (s, 1H), 7.73 (dd, J=7.4, 4.5 Hz, 3H), 4.94 (d, J=5.0 Hz, 2H), 2.69 (s, 3H).

Example 9: Synthesis of Compound VIII

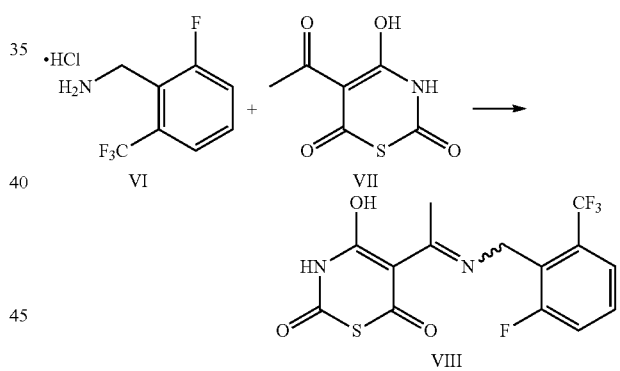

To a 5 L reactor was added IPA (3.2 L), NaOH (70 g), compound VI (400 g) and compound VII (358.7 g). The reaction mixture was heated to 80~90° C. for 2 h. After completion of the reaction, the reaction mixture was cooled to 15~25° C. The resulting suspension was filtered to give the product as a light yellow solid (650 g, 104.5% yield, 98.9% purity).

Example 10: Synthesis of Compound IX

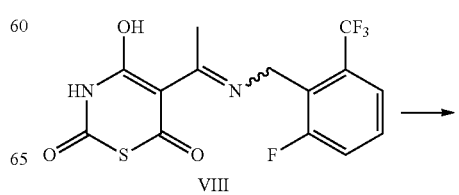

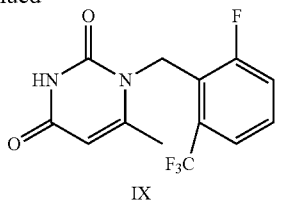

To a 100 mL round-bottom flask was added DMF (25 mL) and compound VIII (5 g). The reaction mixture was heated to 120~130° C. for 8 h. After completion of the reaction, H₂O (50 mL) was added to the reaction mixture. The resulting suspension was filtered to give the product as a light yellow solid (3.44 g, 82.5% yield, 98.0% purity).

¹H NMR (400 MHz, CDCl₃) δ 9.03 (s, 1H), 7.56 (d, J=7.8 Hz, 1H), 7.46-7.41 (m, 1H), 7.30-7.25 (m, 1H), 5.61 (s, 1H), 5.38 (s, 2H), 2.17 (s, 3H).

Mass: [M+H]⁺: 303.1;

Example 11: Synthesis of Compound IX

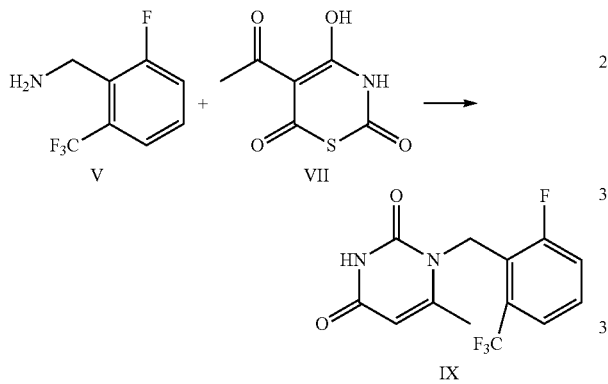

To a 50 mL round bottom flask was added DMF (5 mL), compound V (1 g) and compound VII (1.07 g). The reaction mixture was heated to 140° C. for 0.5 h. After completion of the reaction, H₂O (15 mL) was added to the reaction mixture at 50~60° C. The resulting suspension was filtered. The cake was washed with EtOH (1 mL) to give the product as a white solid (1.05 g, 67% yield, 98.6% purity).

Example 12: Synthesis of Compound X

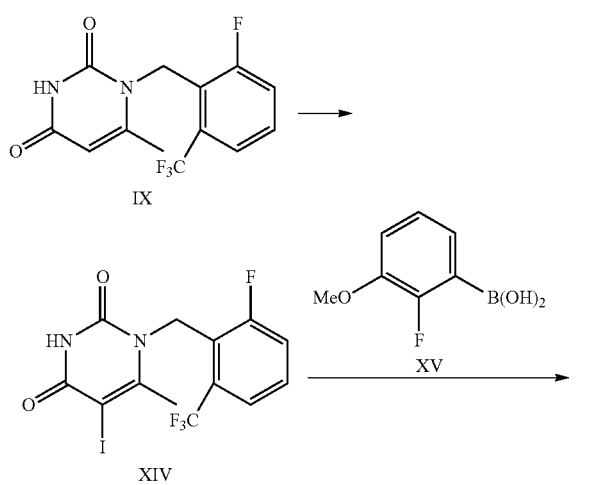

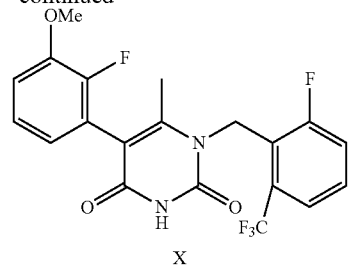

To a 50 mL round bottom flask was added AcOH (20 mL), compound IX (2 g) and N-Iodosuccinimide (1.5 g). The reaction mixture was heated to 50° C. for 1 h. After completion of the reaction, H₂O (10 mL) was added to the reaction mixture. The resulting suspension was filtered. The cake was washed with MeOH (4 mL). The solid was slurried with MeOH (20 mL) to give the product as a white solid (2.3 g, 82% yield, 96.1% purity).

¹H NMR (400 MHz, DMSO-d6) δ 11.75 (s, 1H), 77.67-7.61 (m, 1H), 7.59-7.50 (m, 2H), 5.39 (s, 1H), 2.56 (s, 3H).

To a 1.0 L reactor was added compound XIV (30 g), compound XV (13.1 g), acetone (90 mL) and 14.4% KOH solution (113 g). The reaction mixture was degassed with N₂ for 1 h. Methanesulfonato tri(tert-butyl)phosphine (2'-amino-1,1'-biphenyl-2-yl) palladium (II) (200 mg) was added. The reaction mixture was stirred at 50° C. After completion of the reaction, AcOH (8.4 g) was added. The resulting suspension was filtered. The cake was washed with H₂O (60 mL) and MeOH (120 mL) to give the product as an off-white solid (21.6 g, 72.3% yield, 98% purity).

¹H NMR (400 MHz, DMSO-d6) δ 11.59 (s, 1H), 7.67-7.65 (m, 1H), 7.59-7.56 (m, 2H), 7.17-7.13 (m, 2H), 6.76-6.72 (m, 1H), 5.34 (s, 2H), 3.85 (s, 3H), 2.05 (s, 3H).

Example 13: Synthesis of Compound XII

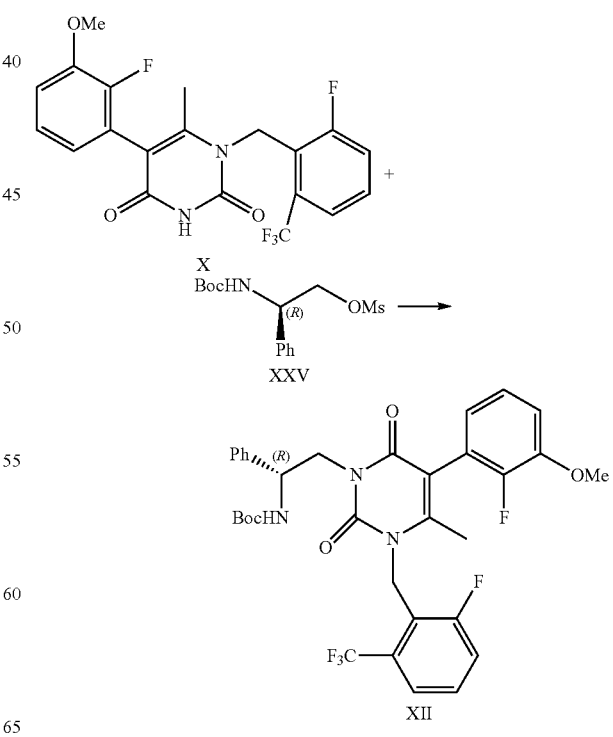

To a 50 mL round bottom flask was added DMF (9 mL), compound X (1.5 g), potassium carbonate (1.22 g) and compound XXV (1.44 g). The reaction mixture was stirred at 55° C. for 16 h. After completion of the reaction, H₂O was added to the reaction mixture. The mixture was extracted with IPAC. The organic phase was concentrated to dryness. The crude product was purified by silica gel column chromatography eluting with IPAC/heptane to give the product (1.65 g, 86% yield, 92% purity).

¹H NMR (400 MHz, CDCl₃) δ 7.58 (d, J=7.9 Hz, 1H), 7.43 (m, 3H), 7.34 (t, J=7.4 Hz, 2H), 7.31-7.23 (m, 2H), 7.16 (t, J=8.0 Hz, 1H), 7.01 (t, J=8.1 Hz, 1H), 6.86 (t, J=6.9 Hz, 1H), 5.78 (t, J=8.4 Hz, 1H), 5.62 (m, 1H), 5.45 (m, 1H), 5.13 (m, 1H), 4.37 (m, 1H), 4.13 (m, 1H), 3.92 (s, 3H), 2.10 (s, 3H), 1.37-1.17 (m, 9H).

Mass: [M+H-Boc]⁺546.1

Example 14: Synthesis of Compound XII

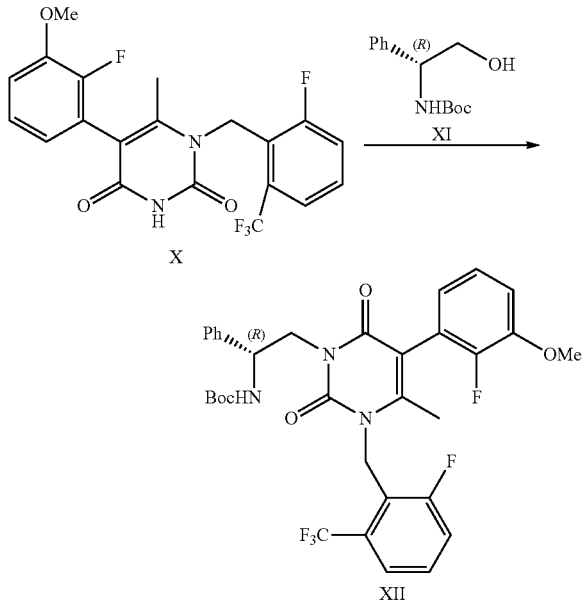

To a mixture of THF (150 mL), compound X (10.0 g), compound XI (6.97 g), and PPh₃ (9.23 g) in a 250 mL round-bottom flask, diisopropyl azodicarboxylate (7.12 g) was added dropwise at 20~30° C. After completion of the reaction, HPLC showed the desired product XII formed.

Example 15: Synthesis of Compound XIII

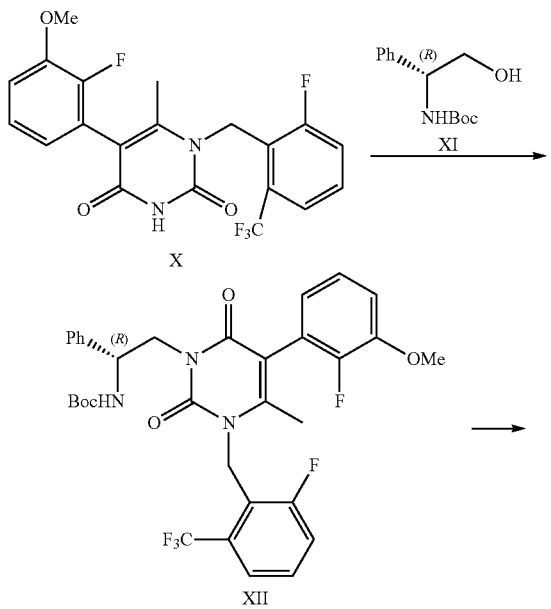

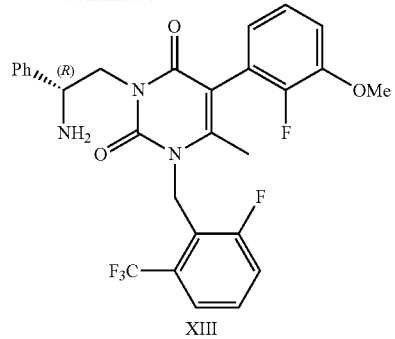

To a mixture of THF (3.0 L), compound X (200.0 g), compound XI (139.1 g), and PPh₃ (184 g) in a 5 L reactor was added diisopropyl azodicarboxylate (142 g) dropwise at 20~30° C. After 1 h, conc. HCl (187.6 g) was added. The reaction mixture was heated and stirred at 50~60° C. After completion of the reaction, the mixture was concentrated to 1 L. IPAC and potassium carbonate aqueous solution was added. The layers were separated. The organic layer was added H₃PO₄ solution. The layers were separated. The aqueous phase was washed with IPAC for 3 times. The pH of the aqueous phase was adjusted to 8~9 with potassium carbonate aqueous solution. The mixture was extracted with IPAC. The organic phase was concentrated. The crude product was recrystallized with IPAC/heptane to give the product as a white solid (210 g, 82.1% yield, 99.8% purity)

¹H NMR (400 MHz, DMSO-d6) δ 7.67-7.65 (m, 1H), 7.59-7.53 (m, 2H), 7.29-7.25 (m, 4H), 7.20-7.14 (m, 3H), 6.76-6.61 (m, 1H), 5.35-5.33 (m, 2H), 4.12-4.10 (m, 1H), 3.96-3.89 (m, 2H), 3.86 (s, 3H), 2.10 (s, 3H).

Mass: [M+H]⁺546.2.

We claim:

1. A process of making the compound elagolix or elagolix sodium comprising:
converting a compound of formula VIII to a compound of formula IX in an organic solvent

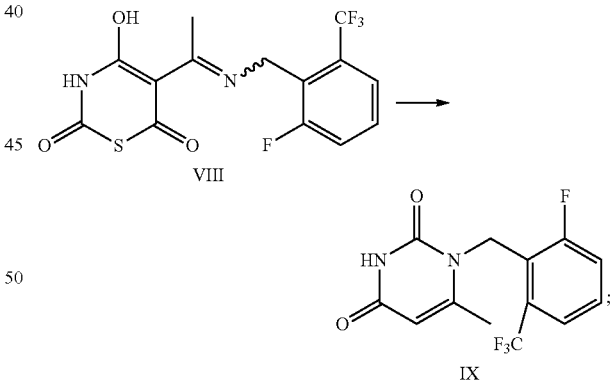

and
converting the compound of formula IX to the elagolix or elagolix sodium.

2. The process of claim 1 wherein the organic solvent is selected from the group consisting of dimethylformamide, dimethylacetamide, acetonitrile, n-butanol, tert-butanol, 1,4-dioxane, dimethyl sulfoxide, N-methylpyrrolidone, sulfolane, and mixtures thereof.

3. The process of claim 1, wherein the organic solvent is dimethylformamide or N-methylpyrrolidone.

4. The process of claim 1 wherein the step of converting the compound of formula IX to the elagolix or elagolix sodium comprises:

reacting the compound of formula IX with N-iodosuccinimide in the presence of acetic acid to obtain a compound of formula XIV, and reacting the compound of formula XIV with a compound of formula XV in the presence of methanesulfonato[tri(tert-butyl) phosphine (2'-amino-1,1'-biphenyl-2-yl)]palladium (II) as a catalyst to obtain the compound of formula X:

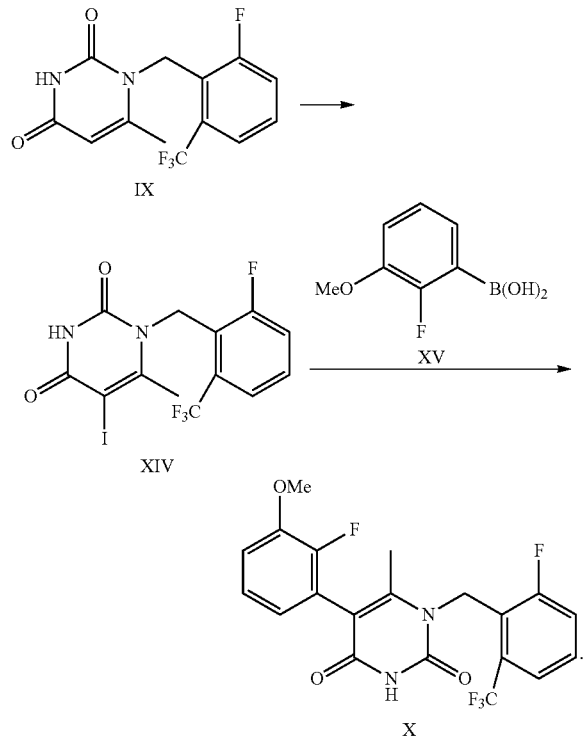

5. The process of claim 4 wherein the step of converting the compound of formula IX to the elagolix or elagolix sodium further comprises:

reacting the compound of formula X with a compound of formula XI in a solvent to make a compound of formula XII:

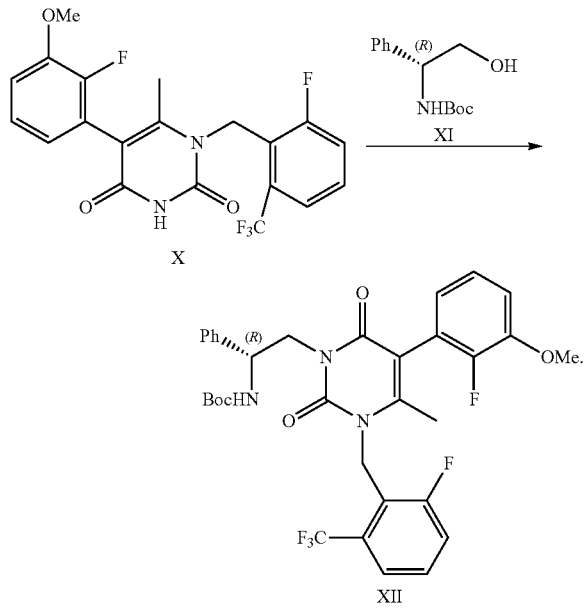

6. The process of claim 5, wherein the solvent is selected from the group consisting of dichloromethane, toluene, 1,4-dioxane, tetrahydrofuran, methyltetrahydrofuran, and mixtures thereof.

7. The process of claim 5, wherein the solvent is tetrahydrofuran.

8. The process of claim 5 wherein the step of converting the compound of formula IX to the elagolix or elagolix sodium further comprises:

reacting the compound of formula XII with an acid to make a compound of formula XIII:

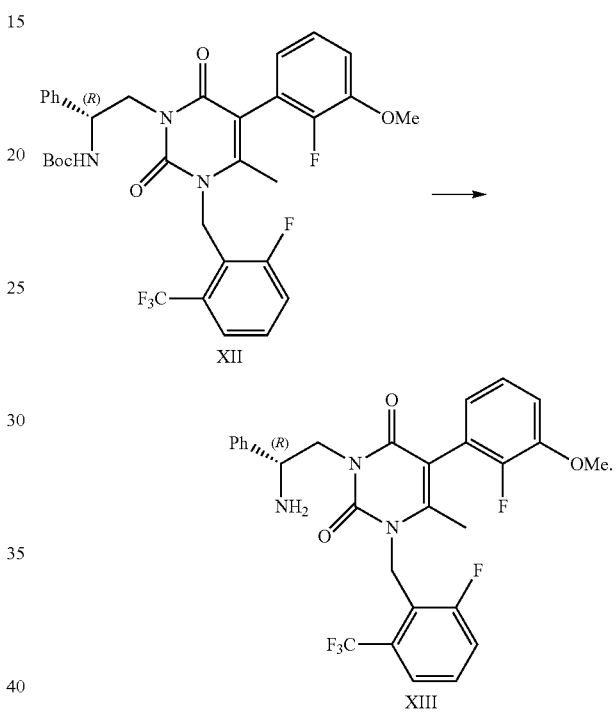

9. The process of claim 8, wherein the acid is hydrochloric acid.

10. The process of claim 4 wherein the step of converting the compound of formula IX to the elagolix or elagolix sodium further comprises a one-pot process comprising:

conducting a Mitsunobu reaction of the compound of formula X and a compound of formula XI to produce a compound of formula XII, and an acidic Boc group deprotection of the compound of formula XII to produce a compound of formula XIII:

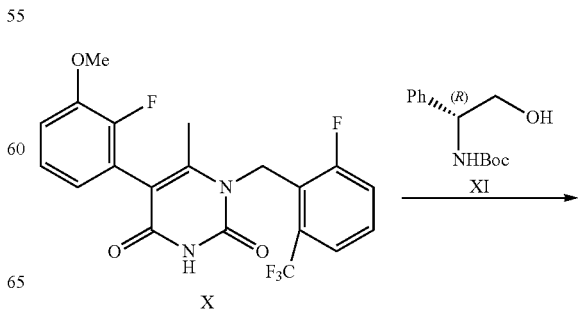

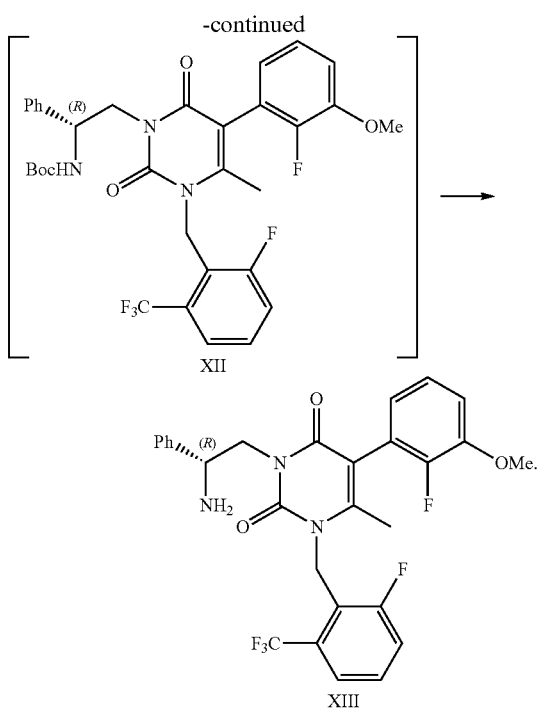

11. The process of claim 10 wherein the acidic deprotection is conducted in the presence of hydrochloric acid.

12. A compound of formula VIII having Z- or E-configuration or mixture of them:

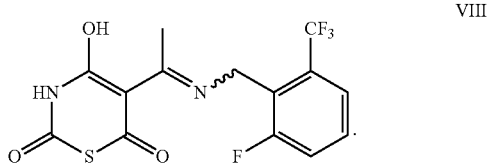 [SMILES: CC(=NCc1c(F)cccc1C(F)(F)F)c1c(O)[nH]c(=O)sc1=O]

13. A process for the preparation of the compound of formula VIII of claim 12 comprising reacting a compound of formula VII with a compound of formula V or a salt thereof in a solvent:

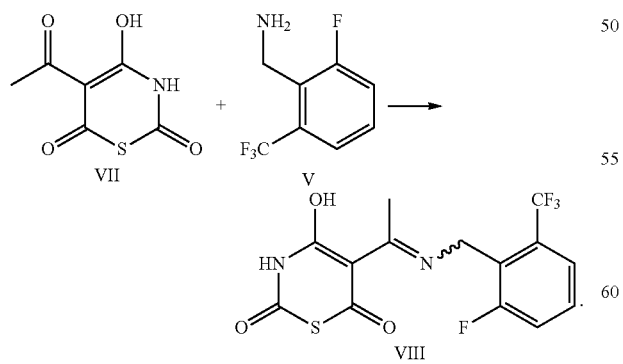

14. The process of claim 13, wherein the solvent is selected from the group consisting of dimethylformamide, dimethylacetamide, acetonitrile, tetrahydrofuran, methyltetrahydrofuran, isopropanol, n-butanol, tert-butanol, 1,4-dioxane, dimethyl sulfoxide, N-methylpyrrolidone, sulfolane and mixtures thereof.

15. The process of claim 13, wherein the solvent is isopropanol.

16. The process of claim 13 comprising reacting a compound of formula IV with an acid to make the compound of formula V or a salt thereof:

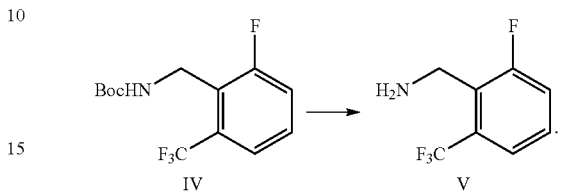

17. The process of claim 16 comprising hydrogenating a compound of formula III in presence of a transition-metal catalyst and di-tert-butyl dicarbonate under $H_2$ atmosphere to produce the compound of formula IV:

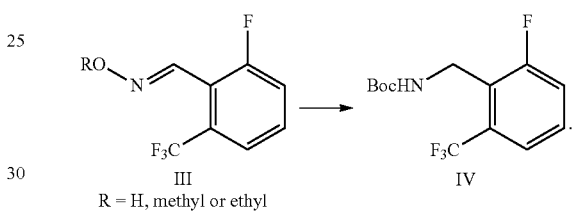

18. The process of claim 17, wherein the transition-metal catalyst is Pd/C or Raney nickel.

19. The process of claim 17 comprising:
conducting formylation of a compound of formula I in the presence of one or more amines and an organolithium reagent to produce a compound of formula II, and
reacting the compound of formula II with hydroxylamine, O-methylhydroxylamine, O-ethylhydroxylamine, a salt of hydroxylamine, a salt of O-methylhydroxylamine, or a salt of O-ethylhydroxylamine, to produce the compound of formula III:

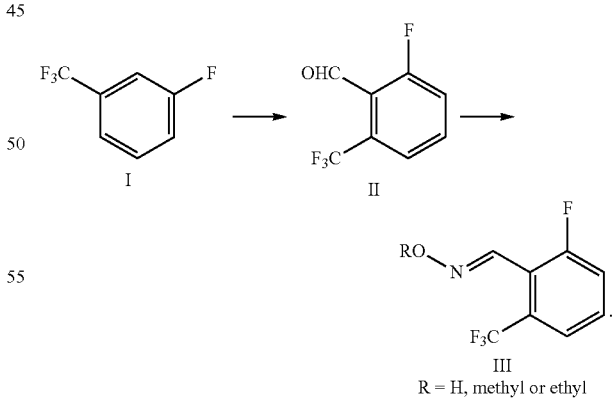

20. The process of claim 19 wherein the amines are selected from the group consisting of tetramethylethylenediamine, diisopropylamine, diethylamine, di-sec-butylamine, pentamethyldiethylenetriamine, and combinations thereof.

* * * * *